US007088455B1

(12) United States Patent
Kirkpatrick et al.

(10) Patent No.: US 7,088,455 B1
(45) Date of Patent: Aug. 8, 2006

(54) METHODS AND APPARATUS FOR MATERIAL EVALUATION USING LASER SPECKLE

(75) Inventors: Sean J. Kirkpatrick, Portland, OR (US); Donald D. Duncan, Silver Spring, MD (US)

(73) Assignee: Providence Health Systems —Oregon, Portland, OR (US)

( * ) Notice: Subject to any disclaimer, the term of this patent is extended or adjusted under 35 U.S.C. 154(b) by 336 days.

(21) Appl. No.: 10/172,754

(22) Filed: Jun. 14, 2002

Related U.S. Application Data (60) Provisional application No. 60/370,927, filed on Apr. 8, 2002.

(51) Int. Cl.
*G01B 11/02* (2006.01)
(52) U.S. Cl. ..................................... 356/502
(58) Field of Classification Search ............... 356/502, 356/487, 508, 511, 512, 513, 35.5, 432, 496, 356/498; 73/1.82, 603
See application file for complete search history.

(56) References Cited

U.S. PATENT DOCUMENTS

| | | | | |
|---|---|---|---|---|
| 3,585,848 A * | 6/1971 | Korpel | ........................ | 73/604 |
| 3,742,439 A * | 6/1973 | Sheridon | ...................... | 367/10 |
| 3,790,281 A * | 2/1974 | Kessler et al. | ................ | 356/72 |
| 3,983,529 A * | 9/1976 | Langlois | ...................... | 367/10 |
| 4,012,951 A * | 3/1977 | Kessler | ........................ | 73/606 |
| 4,526,465 A * | 7/1985 | Corti et al. | ................ | 356/35.5 |
| 4,633,715 A * | 1/1987 | Monchalin | .................... | 73/657 |
| 4,751,686 A * | 6/1988 | Uchino et al. | ................. | 367/7 |
| 5,524,636 A | 6/1996 | Sarvazyan et al. | | |
| 5,546,187 A * | 8/1996 | Pepper et al. | ................ | 356/487 |
| 5,760,904 A * | 6/1998 | Lorraine et al. | ............ | 356/513 |
| 5,806,521 A * | 9/1998 | Morimoto et al. | .......... | 600/447 |
| 6,008,887 A * | 12/1999 | Klein et al. | ................ | 356/28.5 |
| 6,043,870 A * | 3/2000 | Chen | ......................... | 356/35.5 |
| 6,067,859 A | 5/2000 | Käs et al. | | |
| 6,087,652 A * | 7/2000 | O'Meara et al. | ......... | 250/214.1 |
| 6,097,477 A | 8/2000 | Sarrafzadeh-Khoee | | |
| 6,160,826 A * | 12/2000 | Swanson et al. | .............. | 372/20 |
| 6,400,449 B1 * | 6/2002 | Maris et al. | .................. | 356/72 |
| 6,705,993 B1 | 3/2004 | Ebbini et al. | | |
| 6,717,681 B1 | 4/2004 | Bard et al. | | |

OTHER PUBLICATIONS

Kirkpatrick et al., "High resolution imaged laser speckle strain gauge for vascular applications," *Journal of Biomedical Optics* 5:62-71 (Jan. 2000).

(Continued)

*Primary Examiner*—Gregory J. Toatley, Jr.
*Assistant Examiner*—Michael A. Lyons
(74) *Attorney, Agent, or Firm*—Klarquist Sparkman, LLP (57) ABSTRACT

Methods for measuring strains in biological and other samples include illuminating a specimen with substantially collimated laser flux. An electro-acoustic transducer is activated to generate acoustic waves in the specimen, including a surface wave component such as a Rayleigh wave. A series of laser speckle patterns produced by a laser flux scattered or reflected by the specimen is recorded and speckle pattern shifts are calculated based on the recorded speckle patterns. Phase shifts produced by acoustic wave propagation in the specimen are used to identify specimen regions associated with irregularities such as inclusions, cracks, or tissue abnormalities. In some examples, specimens are stretched or otherwise stressed by one or more light fluxes, and specimen elongation is estimated based on a series of associated speckle patterns.

35 Claims, 4 Drawing Sheets

OTHER PUBLICATIONS

Kirkpatrick et al., "Laser speckle microstrain measurement in vascular tissue," *Proc. SPIE* 3598:121-129 (Apr. 1999).

Kirkpatrick et al., "Direct Measurement of Strain Rates in Biological Tissues," *Proc. SPIE* 3914:630-638 (Jun. 2000).

Duncan et al., "Processing techniques for laser speckle derived from biological tissues," *Proc. SPIE* 3914:639-647 (Jun. 2000).

Hinds et al., "Material properties of engineered tissues evaluated with nondestructive methods," *Proc. SPIE* 4617:275-283 (2002).

Kirpatrick et al., "Speckle Tracking of Low-Frequency Surface Acoustic Waves for Mechanical Characterization of Tissues," Proc. SPIE 4619:(Jan. 2002).

Guck et al., "The Optical Stretcher: A Novel Laser Tool to Micromanipulate Cells," Biophysical Journal 81:767-784 (Aug. 2001).

Kirkpatrick et al., *Handbook of Optical Biomedical Diagnostics* Ch. 20 (Feb. 2002).

\* cited by examiner

METHODS AND APPARATUS FOR MATERIAL EVALUATION USING LASER SPECKLE

CROSS REFERENCE TO RELATED APPLICATIONS

This application claims priority from Provisional Patent Application 60/370,927, filed Apr. 8, 2002.

STATEMENT REGARDING FEDERALLY SPONSORED RESEARCH

The U.S. government has a paid-up license in this invention and the right in limited circumstances to require the patent owner to license to others on reasonable terms as provided for by the terms of Contract BES-0086719 awarded by the National Science Foundation.

TECHNICAL FIELD

The invention pertains to laser speckle based materials evaluation.

BACKGROUND

Optical non-destructive evaluation (NDE) has been used in numerous materials characterization applications in the aerospace, semiconductor, and other industries. Conventional optical NDE methods are based on speckle interferometry, speckle photography, or double-exposure holography. Speckle-based methods take advantage of the speckle patterns produced by the scattering of monochromatic light, such as a laser light flux, from a rough surface. As a result, laser based optical speckle methods do not require specimen contact to assess specimen properties.

Speckle-based methods tend to be unsuited to measurement of many specimens of interest, frequently because of difficulties associated with either the application of a test stimulus or interrogation of the response to the stimulus. In addition, conventional methods frequently do not provide sufficient measurement resolution. While some optical NDE methods have been used to evaluate biological specimens in medical research applications, these methods are generally unsuitable for clinical applications. For example, clinical strain measurements of biological tissues or cell distortions are especially difficult. Accordingly, improved measurement methods and apparatus are needed.

SUMMARY

Measurement systems for assessing elastic properties of a specimen include an electro-acoustic transducer configured to produce an acoustic wave in the specimen, and a light source configured to deliver a substantially collimated light flux to the specimen to produce a speckle pattern. An image capture device is situated to record a series of speckle patterns and a signal processor receives a series of such recorded speckle patterns and determines a speckle shift associated with the acoustic wave. According to representative examples, the systems include a memory configured to store the series of recorded speckle patterns and a lens configured so that the speckle patterns recorded by the image capture device are imaged speckle patterns. In additional examples, the image capture device records a series of two dimensional speckle patterns and two dimensional speckle shifts are determined for one or more specimen locations. According to other examples, the electro-acoustic transducer is situated to produce a surface acoustic wave such as a Rayleigh wave. In other examples, the signal processor is configured to determine speckle shifts based on a maximum entropy method, a minimum mean squares method, or other method.

Measurement apparatus include at least one light source configured to alternately illuminate a specimen at a first angle of incidence and a second angle of incidence, and produce corresponding first series and second series of speckle patterns. An image capture device is configured to capture the first and second series of speckle patterns. A signal processor determines first and second speckle shifts based on the first and second series of captured speckle patterns. According to representative examples, the first angle of incidence and the second angle of incidence are approximately opposite and equal in magnitude. In representative examples, a two-dimensional strain map is produced based on the speckle shifts as a function of specimen location.

Apparatus for assessing a tissue specimen include a light source configured to illuminate the tissue specimen and produce speckle patterns, and an image capture device configured to record the speckle patterns. An electro-acoustic transducer is configured to produce an acoustic wave and a speckle record processor estimates a speckle shift produced by the acoustic wave. In some examples, the apparatus include an indicator configured to provide an assessment metric based on the speckle shift. In still further examples, the speckle record processor is configured to estimate speckle shifts associated with at least two regions of the tissue specimen, and the assessment metric is based on a comparison of the speckle shifts.

Methods of producing temporally varying speckle patterns include illuminating a specimen with a light flux and generating an acoustic wave in the specimen at an acoustic frequency having an associated acoustic wavelength that is substantially larger than the illuminated region of the specimen. According to representative examples, the acoustic wave is a surface acoustic wave.

Methods of assessing a tissue sample include measuring a first speckle shift associated with a first region of the tissue sample and a second speckle shift associated with a second region of the tissue sample. The first speckle shift and the second speckle shift are compared and an abnormality is indicated based on the comparison. In other examples, the methods include producing speckle patterns associated with the first speckle shifts and the second speckle shifts by propagating an acoustic wave at a frequency of less than about 10 Hz in the tissue sample.

Apparatus for determining specimen distortion include a laser configured to provide component beams directed to the specimen so that the specimen is distorted. A light illuminates the distorted specimen and produces a speckle pattern based on the specimen. An imaging device is configured to record a series of speckle pattern images and a processor provides an estimate of specimen distortion based on the series of speckle patterns. According to representative embodiments, the specimen is a cell and a flow chamber is provided to retain the cell in a fluid flow.

Methods of determining a distortion of a specimen include distorting the specimen with at least one light flux and obtaining a speckle pattern image series based on a speckle pattern produced by the specimen. The specimen distortion is estimated based on the speckle pattern image series. According to representative embodiments, the specimen is distorted using two counter-propagating laser beams. In additional examples, the specimen is trapped using the at least one light flux.

These and other features are set forth below with reference to the accompanying drawings.

DETAILED DESCRIPTION

Figure 1:
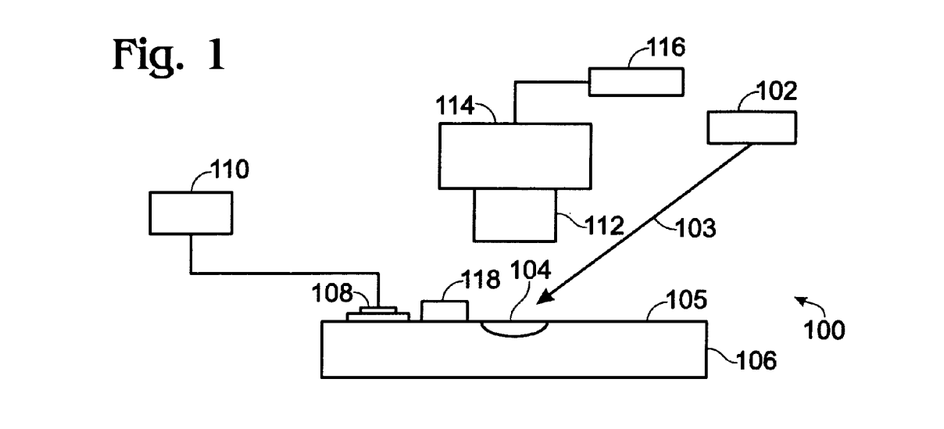
FIG. 1 is a schematic block diagram of a speckle-based measurement system.

With reference to FIG. 1, an optical test system 100 that permits nondestructive materials evaluation includes a laser 102 that delivers a light flux 103 to a region of interest (ROI) 104 of a specimen 106. The light flux 103 can be conveniently delivered to the specimen 106 with an optical fiber, fiber bundle, or other optical waveguide(s) that is configured to receive the light flux 103 from the laser 102 and direct the light flux 103 to the specimen 106. Typically the light flux 103 is substantially collimated as delivered to the specimen 106, but lenses or other optical elements associated with collimation or other beam shaping procedures are not shown in FIG. 1. While beam collimation is convenient, uncollimated light fluxes can also be used.

An electro-acoustic transducer 108 or other acoustic transducer is situated on or near a surface 105 of the specimen 106, and sufficiently close to or in contact with the specimen 106 so that acoustic waves can be generated in at least the region of interest 104. A small speaker can serve as the electro-acoustic transducer 108. A function generator 110 or other electrical signal generator that produces electrical signals suitable for stimulating acoustic waves is electrically connected to the electro-acoustic transducer 108. The function generator typically produces electrical signals of amplitudes of between about 0.1 V and 25 V and at frequencies between about 0.1 Hz and 10 Hz, or at infrasound frequencies between about 1 Hz and 3 Hz. The function generator 110 can be configured to provide various electrical waveforms such as sinusoidal waveforms, triangular waveforms, and square waveforms. Such electrical signals applied to the electro-acoustic transducer 110 tend to produce acoustic waves that propagate in the specimen 106 as surface waves such as Rayleigh waves. Propagation of such surface waves depends on the stiffness of subsurface materials so that subsurface features of the specimen 106 contribute to acoustic propagation characteristics.

A telecentric lens 112 or other lens is situated to receive portions of the light flux reflected or scattered at the region of interest 104 and deliver the received portions to an optical sensor array 114. The sensor array 114 can be a one dimensional array suitable for producing line images or a two dimensional array that can produce two dimensional images. Accordingly, the sensor array 114 provides electrical signals associated with one or two dimensional speckle pattern records (images) to a signal processor 116. Before describing operation of the apparatus 100, some properties of speckle patterns are briefly described.

Speckle Properties

Speckle patterns produced by hydrated tissues (i.e., biological specimens) tend to exhibit decorrelation and are typically at least partially depolarized relative to an incident light flux. Hydrated tissues are generally considered to be adequately described as randomly inhomogeneous media, and the randomness of the tissue structure results in multiple scattering events leading to depolarization. Some tissues are exceptions such as, for example, certain transparent tissues such as eye tissues, mucous membranes, and superficial skin layers. Hydrated tissues tend to swell and shrink, and therefore speckle patterns associated with a particular region of interest tend to change in appearance or decorrelate.

Speckle-based measurements can use first order speckle statistics, second order speckle statistics, or other speckle properties. First order statistics relate to speckle pattern properties at a single point, while second order statistics relate to joint statistical properties of a speckle pattern at two or more points, and can be associated with speckle granularity and speckle size. Mean speckle size in a speckle field depends upon viewing system aperture. For so-called objective (non-imaged) speckle, an effective aperture is a diameter D of a uniformly illuminated area on a scattering surface. Mean speckle diameter $d_{sp}$ at a screen a distance z from a scattering plane is approximately $$d_{sp} \approx 1.2 \lambda_o z / D,$$

wherein $\lambda_o$ is an illumination wavelength. If a lens is used to image a speckle pattern (imaged or so-called subjective speckle), then mean speckle size $d_{sp}$ is approximately $$d_{sp} \approx 2.42 \lambda_o v / 2R_a,$$

where v is a distance from the lens to the imaging plane and $2R_a$ is a diameter of the viewing lens aperture. If a magnification M is provided, then $$d_{sp} \approx 1.2(1+M) \lambda_o v / 2R_a.$$

The above approximations are based on an assumption that the lens images the scattering surface, but such imaging is not required.

In some representative examples, test systems are configured to assess specific specimen responses to an acoustic stimulus. Yamaguchi, "Simplified laser speckle strain gauge," Opt. Eng 21:436–440 (1982), discloses that for an object undergoing strain, speckle shift observed at an angle $\theta_o$ for an illumination angle $\theta_s$ is given by:

$$\delta x(\theta_o, \theta_s) = \alpha_x \left[ \frac{L_o \cos^2 \theta_s}{L_s \cos \theta_o} + \cos \theta_o \right] - \alpha_z \left[ \frac{L_o \cos \theta_s \sin \theta_s}{L_s \cos \theta_o} + \sin \theta_o \right] - \qquad (22)$$

-continued $$L_o\left[\varepsilon_{xx}\left(\frac{\sin\theta_s}{\cos\theta_o}+\tan\theta_o\right)-\Omega_y\left(\frac{\cos\theta_s}{\cos\theta_o}+1\right)\right],$$

wherein $a_x$ is an in-plane motion, $a_z$ is an out-of-plane motion, $\epsilon_{xx}$ is a linear strain in a plane of the detector and laser beams (typically the parameter of interest), $\Omega_y$ is a rotation about an axis perpendicular to the measurement plane, $L_s$ is a radius of an illuminating wavefront (i.e., source distance), and $L_o$ is an observation distance. Using a configuration such as that of FIG. 1 with $\theta_o=0°$ and a collimated light flux ($L_s\to\infty$), and subtracting speckle motions observed at two equal, but opposite illumination angles, a differential speckle shift $\delta A$ is:

$$\delta A \equiv \delta x(0,+\theta_s)-\delta x(0,-\theta_s)=-2L_o\epsilon_{xx}\sin\theta_s.$$

Thus, the in-plane strain term can be isolated. Using a complementary configuration with two cameras and a single illumination angle, $$\delta A \equiv \delta x(+\theta_o,0)-\delta x(-\theta_o,0)=-2L_o\epsilon_{xx}\tan\theta_o-2a_z\sin\theta_o$$

and the desired strain term can be isolated if a term containing $a_z$ is negligible with an appropriate choice of $L_o$ and $\theta_o$.

Referring again to FIG. 1, in operation, an acoustic signal is generated in the specimen 106 by the electro-acoustic transducer 108. Typically the acoustic signal can be represented as a sinusoidal acoustic wave at a frequency between about 0.1 Hz and 10 Hz. Propagation of the acoustic wave in the ROI 104 causes the surface 105 to deform so that a speckle pattern received by the optical sensor 112 varies. The acoustic wave frequency is selected so that an associated acoustic wavelength is longer than a dimension of the ROI 104 so that substantially the entire ROI 104 experiences the same or a similar acoustic stimulus.

Figure 2:
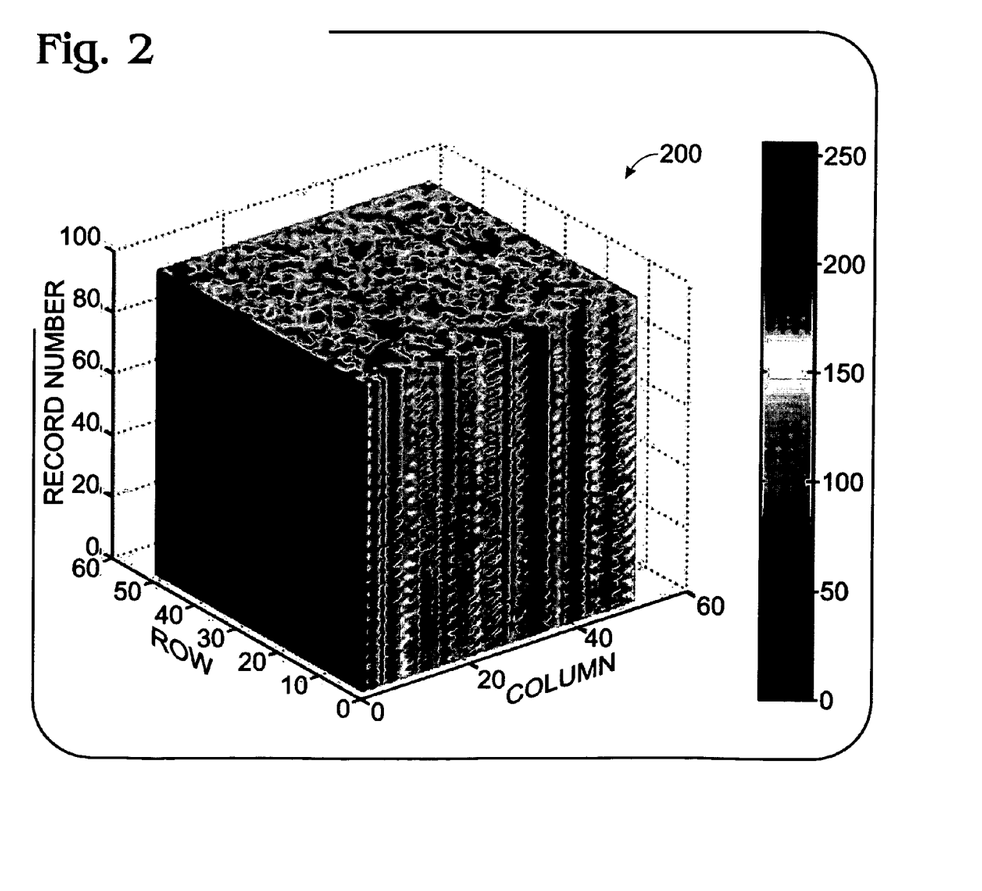
FIG. 2 illustrates sequential two-dimensional speckle records displayed as a stacked speckle history.

Speckle records are captured sequentially. For a two dimensional image sensor, speckle amplitudes $g_{ij}$ of a pixel in an $i^{th}$ row and a $j^{th}$ column are recorded, and the recording process continues until a total $N_{rec}$ of speckle records are captured. A representative two dimensional stacked speckle history 200 is illustrated in FIG. 2. In FIG. 2, speckle amplitudes received by sensor pixels of the image sensor 112 are shown as a function of pixel row and column for a series of sequential speckle records. Speckle amplitudes are represented as gray levels but can be displayed using color grading as well.

Figure 3:
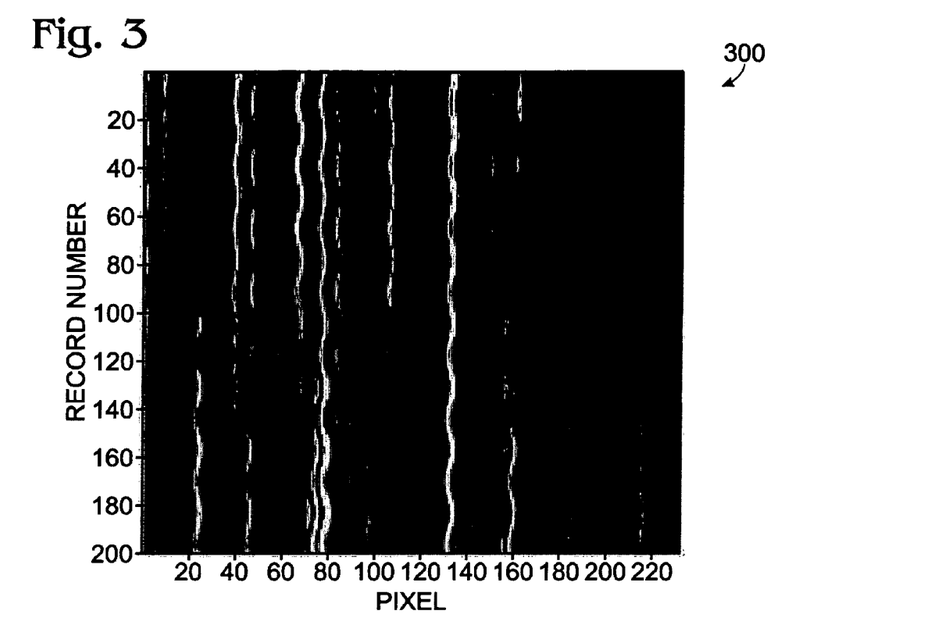
FIG. 3 illustrates sequential one-dimensional speckle records displayed as a stacked speckle history.
Figure 4:
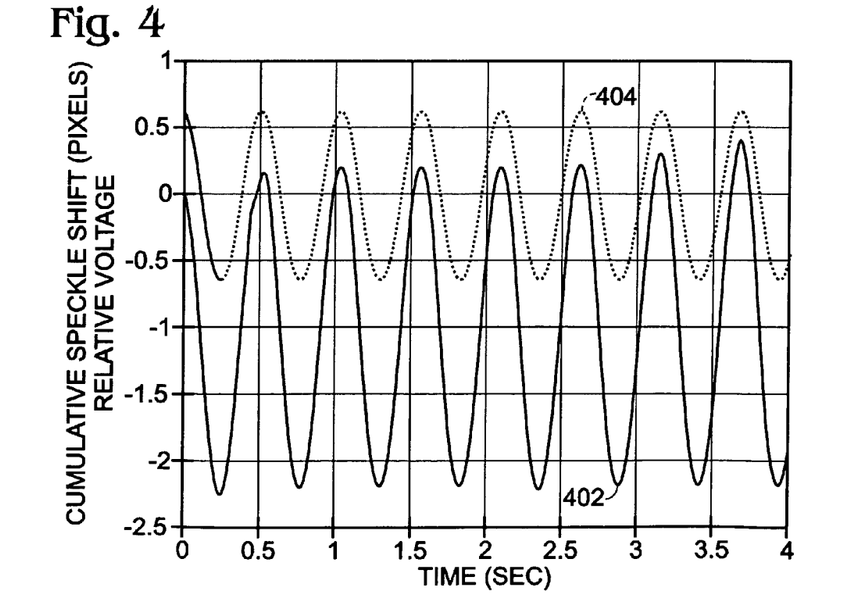
FIG. 4 is a graph of electro-acoustic transducer voltage and speckle shift as functions of time illustrating a phase shift between transducer voltage and speckle shift.

In an example, the apparatus of FIG. 1 was used to assess elastic properties of a porcine skin specimen. The ROI 104 was sinusoidally loaded using a 1 Hz, 20 V peak-to-peak electrical signal applied to the electro-acoustic transducer 108. A 633 nm light flux provided by a helium-neon laser was supplied to the ROI 104 at an angle of incidence of about 45 degrees. Speckle records were captured using 512 pixels of a linear CCD array camera. A total of 200 speckle records were captured with a sample period of 20 ms and an integration time of 10 ms. A representative stacked speckle history 300 is illustrated in FIG. 3. As shown in FIG. 3, pixel amplitudes are shown as gray levels that are functions of row location and record number. Speckle shifts were obtained from the stacked speckle history 300 using a maximum likelihood method that is described below. FIG. 4 illustrates speckle shift and electro-acoustic transducer voltage as functions of time as curves 402, 404, respectively. A phase lag between the transducer voltage and speckle shift was estimated and included a time (phase) correction associated with an acoustic propagation time from the transducer to the ROI based on a phase velocity of about 3.04 m/s. The phase velocity of a Rayleigh wave can be estimated as $C_R\cong 0.92\,C_s$, wherein $C_s$ is a shear wave phase velocity. $C_s$ can be determined by, for example, illuminating two points on a tissue surface as the surface is acoustically stimulated. $C_s$ is then determined by $C_s=\omega L/(\phi_1-\phi_2)$, wherein L is a distance between the two illuminated spots on the tissue surface, $(\phi_1-\phi_2)$ is a difference between a phase of the propagating acoustic wave at the illuminated spots, and $\omega$ is an angular frequency of the surface wave. Such estimation of speckle shifts permits estimation of a phase response of the porcine skin.

The porcine skin specimen was injected with 1 mL of 25% glutaraldehyde to produce artificial lesions of about 1.5 cm diameter at a location 118 between the electro-acoustic transducer 108 and the ROI 104. Loss tangents for untreated and treated porcine skin were obtained in three measurements using ten stacked speckle histories in each measurement. The mechanical loss factor tan $\delta$ for porcine skin decreases significantly with the addition of glutaraldehyde, indicating a reduced contribution by a viscous component of the specimen, reducing energy loss. The table below includes mean values of tan $\delta$ for three sets of ten measurements of untreated and glutaraldehyde-treated porcine skin.

| Trial No. | Untreated | Treated |
|---|---|---|
| 1 | 0.117 +/− 0.041 | 0.031 +/− 0.02 |
| 2 | 0.093 +/− 0.043 | 0.053 +/− 0.025 |
| 3 | 0.154 +/− 0.076 | 0.077 +/− 0.019 |
| Mean | 0.121 +/− 0.053 | 0.054 +/− 0.021 |

Mean values of tan $\delta$ for treated and untreated porcine skin.

While example measurements of a porcine skin specimen are described, clinical measurements can be performed to, for example, assess swelling or identify or characterize tumors or skin lesions, or other specimens can be evaluated. In addition, an unilluminated specimen region can be assessed by directing an acoustic signal through the region and estimating, for example, an acoustic phase shift associated with the region.

Figure 5A:
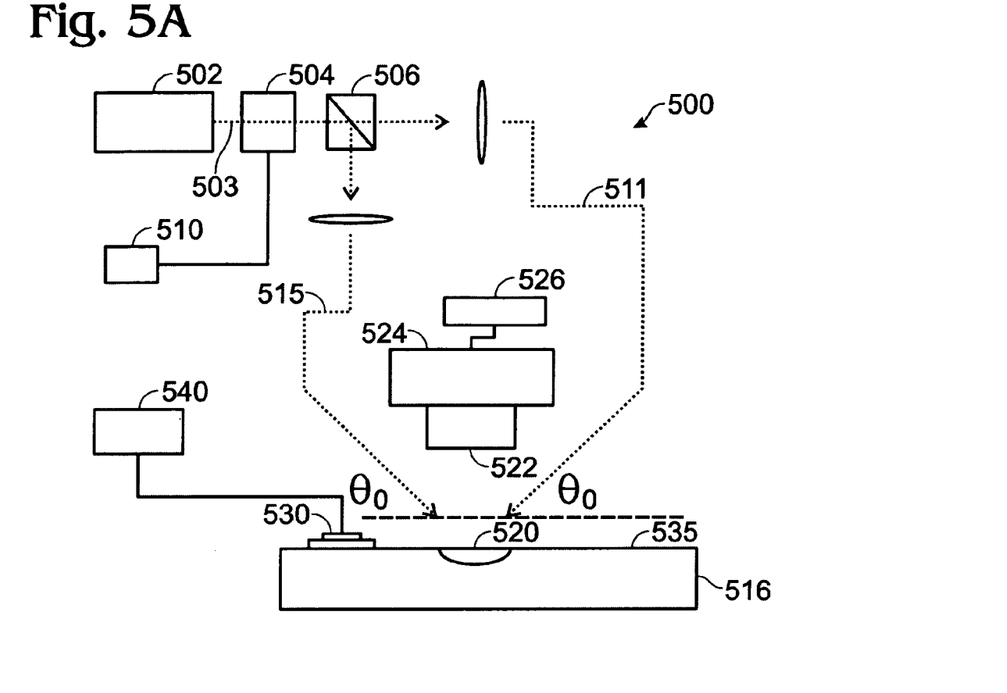
FIG. 5A is a schematic diagram of a measurement apparatus that alternately directs light fluxes to a specimen at different angles of incidence.

Two-dimensional maps of elastic and viscoelastic properties of specimens such as industrial materials, biomaterials, biological tissues, cells, and engineered tissues can be obtained using an optical measurement apparatus 500 illustrated in FIG. 5A. The apparatus 500 includes a laser 502 that delivers a light flux 503 to an electrically switchable half-wave retarder 504 and to a polarizing beamsplitter (PBS) 506. The switchable half-wave retarder 504 can be an electro-optical crystal or the like that is configured to rotate a polarization of the light flux 503 by 90 degrees or to leave the polarization unchanged based on a voltage applied by a controller 510. The PBS 506 typically transmits a parallel (p-polarized) light flux 511 to a beam delivery system such as an optical fiber and associated collimating and focusing lenses. The PBS 506 also typically reflects a perpendicular (s-polarized) light flux 515 to a beam delivery system such as an optical fiber and associated collimating and focusing lenses. Depending on a voltage applied by the controller 510 to the switchable retarder 506, the light flux 503 is delivered to a specimen 516 at an incidence angle of $-\theta_0$, or $\theta_0$, respectively. Other incidence angles can be used, but angles of approximately the same magnitude offer certain advantages as explained above. Other types of switching can be used, and different polarization states can be selected. The light fluxes are generally delivered as collimated light fluxes, but lenses or other components used in collimation are not shown in FIG. 5A.

The light fluxes 511, 515 are thus delivered to a region of interest 520. A lens 522 and a camera 524 receive portions of the light fluxes 511, 515 reflected or scattered by the specimen 516 and deliver electrical signals associated with speckle records to a signal processor 526. An electro-acoustic transducer 530 or other acoustic transducer is situated on or near a surface 535 of the specimen 516, and sufficiently close or in contact with the specimen 516 so that acoustic waves can be generated in at least the region of interest 520. A function generator 540 or other electrical signal generator produces electrical signals suitable for producing acoustic waves and is electrically connected to the electro-acoustic transducer 530.

Figure 5B:
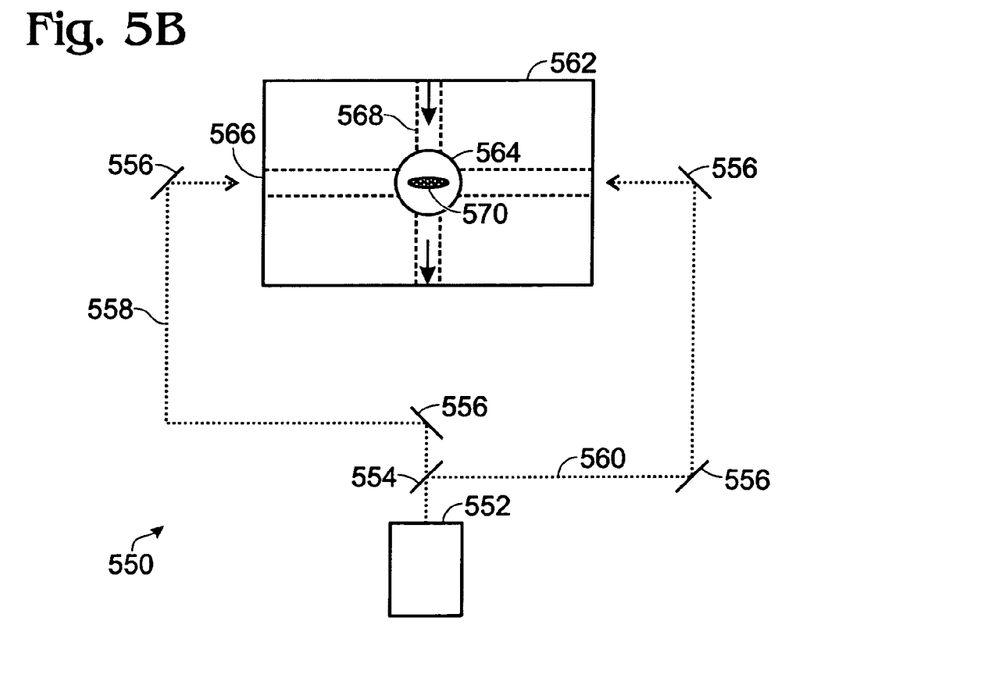
FIG. 5B is a schematic diagram of a measurement apparatus configured to distort a specimen using counter-propagating laser beams.

Alternative methods and apparatus can be used to stress samples. For example, specimens can be stressed in a tensile testing machine. Biological cells or other specimens can be stretched using a laser-based cell stretcher as described in, for example, Guck et al., Biophysical Journal 81:767–784 (2001) and Kas et al., U.S. Pat. No. 6,067,859. Referring to FIG. 5B, a laser-based cell stretcher includes a laser 552 that produces a laser beam that is divided into component beams 558, 560 using a beamsplitter 554. Mirrors 556 direct the beams 558, 560 to a sample stage 562 that includes a flow channel 568 and an optical channel 566. The sample stage 562 is conveniently made of a transparent material. A measurement aperture 564 is situated at an intersection of the flow channel 568 and the optical channel 566, and is configured so that a measurement light flux can be applied to a specimen such as a cell 570. The laser 552 typically provides a pulsed laser beam that can have a variable power, pulse duration, or pulse repetition rate. The laser 552 can be selected to provide radiation at a wavelength suitable for the specimen under investigation or otherwise selected.

The component beams 558, 560 are configured to stretch the cell 570 or other specimen based on applied laser power and pulse repetition rate. The component beams 558, 560 can also be configured to retain or trap the cell 570 in the aperture. Cell deformation or stretching can be evaluated based on speckle pattern shifts as described above with reference to FIG. 1 or FIG. 5A.

The component beams 558, 560 can be conveniently delivered using single mode or multimode optical fibers. Component beam optical power can be modulated using an electro-optic modulator, an acousto-optic modulator, or other optical modulator. Optical power and beam wavelength can be selected so that distortions of living cells can be estimated.

The apparatus 500 of FIG. 5A is similar to the system 100 of FIG. 1, but permits sequential illumination from two opposite, but substantially equal angles. The camera 524 is synchronized with beam switching to generate two stacked speckle histories, one for each of the two incidence angles. Beam delivery with optical fibers permits measurement of specimens with difficult access. The imaging system can also be fiber coupled using, for example, a coherent fiber bundle. An illuminated specimen area can be selected by shaping the beam. From the stacked speckle histories, a pixel-by-pixel analysis can be performed to calculate in-plane strains in a direction of loading. An image can then be constructed based on the magnitude of the strain field and quantitatively display the effects of holes, cracks, inclusions, and other specimen features. This image is two-dimensional strain map. Such a laser speckle-based strain mapping apparatus can produce a strain resolution of better than about 1 part per million, is insensitive to vibration and other zero-mean noise sources, and can be used on hydrated samples such as biological tissues.

Speckle Shift Determination

Speckle shifts can be estimated using several methods. For convenience, these methods can be classified as non-parametric methods or parametric methods. Non-parametric methods generally are not based on assumptions about measured speckle shifts. Representative examples of a non-parametric methods are methods based on cross-correlations of sequential speckle records, in which shifts of correlation peaks between the speckle records are associated with speckle pattern shifts. To improve computational efficiency, cross-correlations are typically calculated using Fourier transforms. Parametric methods include minimum mean square error methods, maximum likelihood methods, and maximum entropy methods. These parametric methods are described below. For convenience in describing these methods, it is assumed that over a time period in which at least a few sequential speckle records are obtained, the structure of the speckle pattern is fixed and the only change with time is a lateral translation of the speckle pattern. In addition, the methods are described below with reference to one dimensional speckle records or two dimensional speckle records.

Minimum Mean Square Error Methods

Speckle motion can be modeled as:

$$g_{j+1}(x_i) = g_j(x_i - \delta x), \quad (1)$$

wherein g is a speckle record pixel value, δx is speckle shift, i denotes an $i^{th}$ pixel in a speckle record, and j represents a speckle record number. For two dimensional speckle records, an additional index can be used. If the speckle shift δx is small compared to pixel size, Eq. (1) can be approximated as $$g_{j+1}(x_i) \approx g_j(x_i) + \delta x g'_j(x_i), \quad (2)$$

corresponding to two terms of a Taylor series expansion for g. For computational convenience, speckle records on either side of a record of interest are selected for evaluation so that terms $$[g_{j+1}(x_i), g_{j-1}(x_i)], \quad (3)$$

are selected. The speckle shift δx is calculated to minimize a mean square error $$\varepsilon_j^2 = \sum_{i=1}^{N} [g_{j+1}(x_i + \delta x) - g_{j-1}(x_i - \delta x)]^2, \quad (4)$$

wherein the summation is performed over all pixels in the speckle records. Eq. (4) can be solved using a gradient search algorithm. Alternatively, using the small speckle motion approximation of Eq. (2), differentiation with respect to δx and rearrangement produces the following relationship:

$$\delta x_j = \frac{-\sum_{i=1}^{N}[g_{j+1}(x_i)-g_{j-1}(x_i)][g'_{j+1}(x_i)+g'_{j-1}(x_i)]}{\sum_{i=1}^{N}[g'_{j+1}(x_i)+g'_{j-1}(x_i)]^2}. \quad (5)$$

The term in the first square bracket in the numerator is a first central difference approximation to a derivative, $$\frac{\partial g_j(x_i)}{\partial t_j} \approx \frac{g_{j+1}(x_i)-g_{j-1}(x_i)}{2}. \quad (6)$$

Spatial derivatives may be approximated as $$\frac{\partial g_{j+1}}{\partial x_i} \approx \frac{g_{j+1}(x_{i+1})-g_{j+1}(x_{i-1})}{2}; \text{ and} \quad (7)$$

$$\frac{\partial g_{j-1}}{\partial x_i} \approx \frac{g_{j-1}(x_{i+1})-g_{j-1}(x_{i-1})}{2}.$$

The speckle shift δx is a time rate at which a speckle pattern shifts in units of pixels/record.

Although the above example method is based on speckle records on either side of a selected record, additional records can be included and their contributions weighted appropriately to estimate higher order approximations. For example, instead of using the weights $$\frac{1}{2}[-1, 0, +1], \quad (8)$$

that correspond to records on either side of a selected record, the weights $$\frac{1}{12}[1, -8, 0, 8, -1] \quad (9)$$

can be used so that two records on either side of the selected record are used. With such weights, the mean square error is:

$$\varepsilon_j^2 = \sum_{i=1}^{N}[g_{j+2}(x_i+2\delta x)-8g_{j+1}(x_i+\delta x)+8g_{j-1}(x_i-\delta x)-g_{j-2}(x_i-2\delta x)]^2, \quad (10)$$

the temporal derivative term of Eq. (5) is $$[-g_{j-2}(x_i)+8g_{j-1}(x_i)-8g_{j+1}(x_i)+g_{j+2}(x_i)] \approx 12\frac{\partial g_j(x_i)}{\partial t_j}, \quad (11)$$

and the term involving spatial derivatives is $$[-2g'_{j-2}(x_i)+8g'_{j-1}(x_i)+8g'_{j+1}(x_i)-2g'_{j+2}(x_i)]. \quad (12)$$

Note that this is simply a weighted average, $$12\left\{\frac{4}{3}\left[\frac{g'_{j-1}+g'_{j+1}}{2}\right]-\frac{1}{3}\left[\frac{g'_{j-2}+g'_{j+2}}{2}\right]\right\} \quad (13)$$

of terms on either side of the selected record. These higher order operators for the derivative can be used to estimate the spatial derivatives:

$$\frac{\partial g_j(x_i)}{\partial x_i} \approx \frac{1}{12}[-g_j(x_{i-2})+8g_j(x_{i-1})-8g_j(x_{i+1})+g_j(x_{i+2})]. \quad (14)$$

The higher order approximations to the derivative typically exhibit superior noise rejection but at the expense of reduced temporal resolution.

The only a priori assumption used in the above methods is that the speckle shift is small with respect to the pixel size. If it is further assumed that measured speckle records include a deterministic speckle signal component and a noise component, the measured signal can be modeled as $$d_j(x_i)=g_j(x_i)+n_j(x_i), \quad (15)$$

wherein n is a zero-mean noise signal. If the central difference about the $j^{th}$ record is calculated, $$d_{j+1}(x_i+\delta x)-d_{j-1}(x_i-\delta x)=g_{j+1}(x_i+\delta x)-g_{j-1}(x_i-\delta x)+n_{j+1}(x_i+\delta x)-n_{j-1}(x_i-\delta x). \quad (16)$$

Sequential speckle patterns are assumed to have a constant mean and the noise is a assumed to be a statistically independent Gaussian random variable with zero mean and constant variance. As a result the noise probability density function can be written as $$p(d_j|g_j)=p(n_j)=C\exp\left\{\frac{-1}{2\sigma^2}\sum_{i=1}^{N}[g_{j+1}(x_i+\delta x)-g_{j-1}(x_i-\delta x)]^2\right\}, \quad (17)$$

wherein C is a constant. Equation (17) is referred to as a likelihood function. To choose the δx that maximizes this likelihood, the following equation is solved:

$$\frac{\partial}{\partial(\delta x)}\ln p(d_j|g_j)=0. \quad (18)$$

Carrying out this calculation leads to the formula in Eq. (5). It can be shown that this provides an unbiased estimate of the speckle pattern shift and that the variance of the estimate attains the Cramér-Rao lower bound.

Entropy Based Methods

Additional methods are based on maximum entropy estimators. Speckle motion is modeled as $$g_{j+1}(x_i) = g_j(x_i - \delta x), \quad (19)$$

wherein the index j denotes a speckle record number and the index i denotes a selected pixel in the speckle record. According to Eq. (19), the difference between speckle records j and j+1 is that the latter is shifted by δx. A shift parameter can be estimated by shifting a pair of records in opposite directions and forming a quotient R of the shifted records, i.e.

$$R_j(x_i) = \frac{g_{j-1}(x_i - \delta x)}{g_{j+1}(x_i + \delta x)}. \quad (20)$$

An entropy parameter H is then calculated as follows:

$$H_j(\delta x) = -\sum_{i=1}^{N} p_j(x_i) \log[p_j(x_i)], \quad (21)$$

wherein $$p_j(x_i) = \frac{R_j(x_i)}{\sum_{i=1}^{N} R_j(x_i)}. \quad (22)$$

Using the normalization of Eq. (22), $$\sum_{i=1}^{N} p_j(x_i) = 1. \quad (23)$$

By maximizing the entropy parameter H of Eq. (21), a shift parameter can be selected that most nearly shifts the numerator and denominator of Eq. (20) into registration to produce a maximally flat quotient. If the distribution p is perfectly flat, the associated entropy is simply log(N). A gradient search algorithm can be used to estimate the shift parameter.

Speckle pattern records generally are interpolated to determine shifted speckle patterns. This interpolation is conveniently performed using the Fourier shift theorem:

$$g_j(x_i - \delta x) = F^{-1}\{e^{-j2\pi\delta x f_k} G_j(f_k)\}, \quad (24)$$

wherein $$G_j(f_k) = F\{g_j(x_i)\}, \quad (25)$$

and F and $F^{-1}$ refer to Fourier transforms and inverse Fourier transforms, respectively. The ratio of Eq. (20) can be obtained as $$R_j(x_i) = \frac{F^{-1}\{e^{-j2\pi\delta x f_k} F\{g_{j-1}(x_i)\}\}}{F^{-1}\{e^{+j2\pi\delta x f_k} F\{g_{j+1}(x_i)\}\}}. \quad (26)$$

Such methods determine values of δx that make this ratio the "flattest." (Other methods such as those based on Eq. 4 can also be made more efficient using the Fourier shift theorem and a gradient search algorithm without assuming that speckle shifts are small.) As implemented, the innermost transforms are computed only once, so that at each iteration of a gradient search, only the following is computed:

$$R_j(x_i) = \frac{F^{-1}\{e^{-j2\pi\delta x f_k} G_{j-1}(f_k)\}}{F^{-1}\{e^{+j2\pi\delta x f_k} G_{j+1}(f_k)\}}. \quad (27)$$

Since the model of Eq. (19) is only approximate, there are occasional noisy spikes in the ratio calculated as in Eq. (20). To avoid the possibility of the gradient search algorithm being trapped in a local maximum, a median filter is applied to the ratio prior to normalization and computation of entropy so that an entropy surface is convex. The gradient algorithm can also be modified to use any a priori knowledge of the amount of speckle record shift. For example, the gradient search can be restricted to a limited range of values. Alternatively, methods can be based on obtaining a minimum value of negative entropy.

Two Dimensional Methods

Figure 6A:
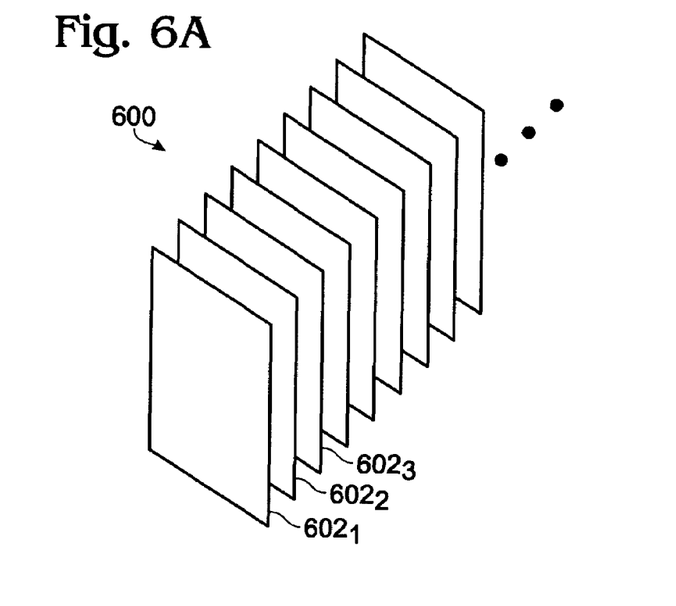
FIG. 6A illustrates a series of stacked speckle images.
Figure 6B:
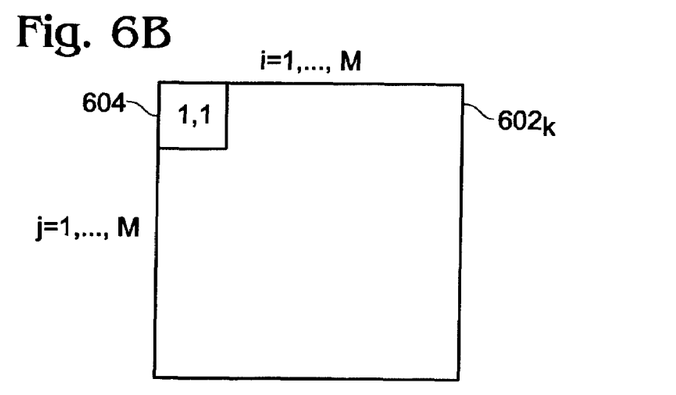
FIG. 6B illustrates a selected speckle image.
Figure 6C:
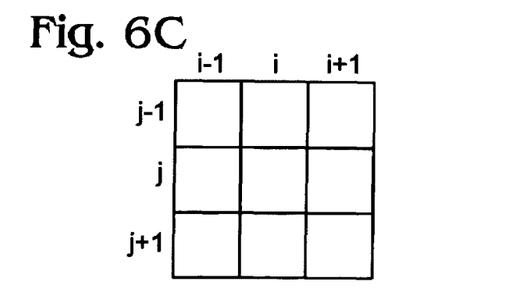
FIG. 6C illustrates a portion of the speckle image of FIG. 6B.

With reference to FIG. 6A, a speckle image series 600 of speckle images $602_1$, $602_2$, ..., is captured. Object motion can be assessed based on image-to-image changes in the speckle image series 600. For convenience in describing processing of the speckle image series 600, a representative speckle image $602_k$ is selected as illustrated in FIG. 6B. A time progression of lateral image shifts associated with this image can be estimated based on, for example, a pair of images adjacent to the $k^{th}$ image, i.e., the speckle images $602_{k-1}$, $602_{k+1}$. A mean square difference between portions of these images is defined as:

$$\varepsilon_k^2 = \sum_i \sum_j [g_{k+1}(x_i + \delta_x, y_j + \delta_y) - g_{k-1}(x_i - \delta_x, y_j - \delta_y)]^2, \quad (28)$$

wherein ($\delta_x, \delta_y$) are x- and y-displacements, $g_{k-1}$, g, $g_{k+1}$ are pixel values associated with the speckle images $602_{k-1}$, $602_k$, $602_{k+1}$, respectively, and $x_i$, $y_j$, are pixel spatial coordinates. The summations are generally performed over, for example, a small subset of pixel values, typically pixel values associated with an array of about 3 pixels by 3 pixels as illustrated in FIG. 6C.

Displacements ($\delta_x, \delta_y$) are estimated such that features in the selected speckle images are brought approximately into registration. Pixel values can be represented as follows using a two-dimensional Taylor series expansion:

$$g(x, y) = g(a, b) + (x - a)\frac{\partial g}{\partial x}\Big|_{\substack{x=a\\y=b}} + (y - b)\frac{\partial g}{\partial y}\Big|_{\substack{x=a\\y=b}} + \qquad (29)$$
$$\frac{1}{2}\left\{(x - a)^2\frac{\partial^2 g}{\partial x^2}\Big|_{\substack{x=a\\y=b}} + 2(x - a)(y - b)\frac{\partial^2 g}{\partial x \partial y}\Big|_{\substack{x=a\\y=b}} + (y - b)^2\frac{\partial^2 g}{\partial y^2}\Big|_{\substack{x=a\\y=b}}\right\} + \ldots$$

Assuming that feature shifts are small, the approximations $$g_{k+1}(x_i + \delta_x, y_j + \delta_y) \approx g_{k+1}(x_i, y_j) + \delta_x \frac{\partial g_{k+1}}{\partial x} + \delta_y \frac{\partial g_{k+1}}{\partial y} \qquad (30)$$

$$g_{k-1}(x_i + \delta_x, y_j + \delta_y) \approx g_{k-1}(x_i, y_j) - \delta_x \frac{\partial g_{k-1}}{\partial x} - \delta_y \frac{\partial g_{k-1}}{\partial y}$$

can be used, and the expression for the mean square error becomes:

$$\varepsilon_k^2 = \sum_i \sum_j \{[g_{k+1}(x_i, y_j) - g_{k-1}(x_i, y_j)] + \qquad (31)$$
$$\delta_x \frac{\partial}{\partial x}[g_{k+1}(x_i, y_j) + g_{k-1}(x_i, y_j)] +$$
$$\delta_y \frac{\partial}{\partial y}[g_{k+1}(x_i, y_j) + g_{k-1}(x_i, y_j)]\}^2.$$

For convenience, the following definitions are used:

$$T = [g_{k-1}(x_i, y_j) - g_{k+1}(x_i, y_j)] \qquad (32a)$$
$$X = \frac{\partial}{\partial x}[g_{k+1}(x_i, y_j) + g_{k-1}(x_i, y_j)]$$
$$Y = \frac{\partial}{\partial y}[g_{k+1}(x_i, y_j) + g_{k-1}(x_i, y_j)].$$

Using these definitions, the equations $$\frac{\partial \varepsilon_k^2}{\partial \delta_x} = 0; \quad \frac{\partial \varepsilon_k^2}{\partial \delta_y} = 0, \qquad (32b)$$

produce a set of simultaneous equations:

$$\begin{vmatrix} \sum_i \sum_j X^2 & \sum_i \sum_j XY \\ \sum_i \sum_j XY & \sum_i \sum_j Y^2 \end{vmatrix} \begin{vmatrix} \delta_x \\ \delta_y \end{vmatrix} = \begin{vmatrix} \sum_i \sum_j TX \\ \sum_i \sum_j TY \end{vmatrix}. \qquad (32c)$$

This set of equations can be inverted to obtain the displacement estimates $(\delta_x, \delta_y)$:

$$\delta_x = \frac{1}{\Delta} det \begin{vmatrix} \sum_i \sum_j TX & \sum_i \sum_j XY \\ \sum_i \sum_j TY & \sum_i \sum_j Y^2 \end{vmatrix} \qquad (32d)$$

$$\delta_y = \frac{1}{\Delta} det \begin{vmatrix} \sum_i \sum_j X^2 & \sum_i \sum_j TX \\ \sum_i \sum_j XY & \sum_i \sum_j TY \end{vmatrix}, \text{ wherein}$$

$$\Delta = det \begin{vmatrix} \sum_i \sum_j X^2 & \sum_i \sum_j XY \\ \sum_i \sum_j XY & \sum_i \sum_j Y^2 \end{vmatrix}. \qquad (32e)$$

The arrays of Equations 32c–32e are N×M arrays and displacement estimates can be produced for every pixel or selected pixels.

Spatial gradients can be calculated based on, for example, a central difference formula so that $$\frac{\partial g_{k+1}(x_i, y_j)}{\partial x} = \frac{g_{k+1}(x_{i+1}, y_j) - g_{k+1}(x_{i-1}, y_j)}{2}. \qquad (33)$$

The indicated summations, for each sub-element of the image pairs, can be calculated using convolution operations. For example, a (1,1) element of the system matrix in Eq. 32c can be as:

$$\sum_i \sum_j X^2 = \left\{(g_{k+1} + g_{k-1}) * \begin{bmatrix} \frac{1}{2} & 0 & -\frac{1}{2} \end{bmatrix}\right\}^2 * \begin{bmatrix} 1 & 1 & 1 \\ 1 & 1 & 1 \\ 1 & 1 & 1 \end{bmatrix}. \qquad (34)$$

In this equation, the squaring operation is performed element-by element. The result of the convolution operations is a matrix that grows in height by three elements and width by six elements. The additional pixels can be discarded. Similarly, $$\sum_i \sum_j Y^2 = \left\{(g_{k+1} + g_{k-1}) * \begin{bmatrix} \frac{1}{2} \\ 0 \\ -\frac{1}{2} \end{bmatrix}\right\}^2 * \begin{bmatrix} 1 & 1 & 1 \\ 1 & 1 & 1 \\ 1 & 1 & 1 \end{bmatrix}. \qquad (35)$$

In Equations 34–35, the first convolution is with a derivative operator and the second convolution performs a local sum.

In the example of Equations 34–35, derivatives are obtained based on a central difference estimate, but in additional examples, optimized derivative filters or other methods can be used. The operations of Equations 34–35 can extend matrix height and width by three rows and three columns, but these additional values can be discarded.

Methods and apparatus for quantitative imaging of elastic and viscoelastic properties of materials such as human tissues and cells based on stacked speckle histories can provide surface maps of simple and complex plane strains. Two-dimensional maps of speckle shifts quantitatively describe, for example, an in-plane strain field in a test specimen. Regions with large or small strains can be imaged and mapped to identify, for example, inhomogeneities such as a subsurface defect, or a subdermal lesion, other pathological tissue, or other specimen feature.

As shown above, by applying a selected stress (acoustic wave) to a specimen, spatially resolved elastic constants of the specimen such as, for example, Young's modulus, can be obtained. Based on a phase of an applied stress, a mechanical loss factor (tan $\delta$) and other derived viscoelastic properties can be evaluated. Two-dimensional strain fields can be image and evaluated using apparatus such as shown in FIG. 1 and FIGS. 5A–5B, and specimens such as human tissues, metals, plastics, ceramics, or other materials can be selected. Strain resolutions of at least 1 $\mu\varepsilon$ (microstrain) can be obtained, and spatial resolutions can be selected based on imaging optics resolution. Strain mapping of objects as small as cells (~10 microns) or objects having dimensions as large as a few meters can be performed, and strain images of still smaller and larger objects can be obtained. Variations in elastic properties of a specimen are readily detected and because abnormal tissue frequently is "softer" than normal tissue, abnormal tissue can be identified.

Examples are described above but can be changed in arrangement and detail without departing from the claimed subject matter. For example, illumination sources of different wavelengths can be used, and one, two, or more illumination sources can be provided in a single apparatus. Illumination can be provided to specimens at two equal and opposite angles or at two different angles. Acoustic frequency can be varied and speckle record acquisition rates can be increased or decreased. We claim all that is encompassed by the appended claims.

The invention claimed is:

1. An apparatus for assessing elastic properties of a specimen, comprising:
an electro-acoustic transducer configured to produce an acoustic wave in the specimen;
a light source configured to deliver a light flux to the specimen and produce an optical speckle pattern that is recorded by an image capture device; and
a signal processor configured to receive a series of recorded optical speckle patterns and determine an optical speckle shift associated with the acoustic wave based on estimating shifted values of portions of at least two recorded optical speckle patterns.

2. The apparatus of claim 1, further comprising a memory configured to store the series of recorded optical speckle patterns.

3. The apparatus of claim 1, further comprising a lens configured so that the optical speckle pattern recorded by the image capture device is an imaged optical speckle pattern.

4. The apparatus of claim 1, wherein the image capture device records two-dimensional optical speckle patterns.

5. The apparatus of claim 4, wherein the signal processor is configured to determine optical speckle shifts associated with a plurality of specimen locations.

6. The apparatus of claim 1, wherein the acoustic wave produced by the electro-acoustic transducer includes a surface acoustic wave.

7. The apparatus of claim 1, wherein the signal processor is configured to determine the optical speckle shift based on a sum of a ratio of corresponding estimated shifted values of the portions of the at least two recorded optical speckle patterns.

8. The apparatus of claim 1, wherein the signal processor is configured to determine the optical speckle shift based substantially minimizing a sum of a square of differences between corresponding estimated shifted values of the portions of the at least two recorded optical speckle patterns.

9. The apparatus of claim 1, wherein the signal processor estimates the shifted values of the portions of the at least two recorded optical speckle patterns based on products of trial values of the estimated speckle shift and estimated values of derivatives of recorded values of the optical speckle patterns.

10. An apparatus, comprising:
at least one light source configured to alternately illuminate a specimen at a first angle of incidence and a second angle of incidence, and produce a first series of optical speckle patterns and a second series of optical speckle patterns;
an image capture device configured to capture the first and second series of optical speckle patterns; and
a signal processor configured to determine first and second speckle shifts based on the first and second series of recorded optical speckle patterns based on interpolated speckle shifts obtained from the recorded optical speckle patterns.

11. The apparatus of claim 10, wherein the first angle of incidence and the second angle of incidence are approximately equal and opposite.

12. An apparatus for assessing a tissue specimen, comprising:
a light source configured to illuminate the tissue specimen and produce optical speckle patterns;
an image capture device configured to record the optical speckle patterns;
an electro-acoustic transducer configured to produce an acoustic wave;
a speckle record processor configured to determine estimated shifted speckle patterns for at least portions of the recorded optical speckle patterns, and to estimate speckle shifts in the optical speckle patterns produced by the acoustic wave based on the estimated shifted speckle patterns.

13. The apparatus of claim 12, further comprising an indicator configured to provide an assessment metric based on the speckle shift.

14. The apparatus of claim 13, wherein the speckle record processor is configured to estimate speckle shifts associated with at least two regions of the tissue specimen and the assessment metric is based on a comparison of the speckle shifts.

15. The apparatus of claim 12, wherein the speckle record processor is configured to estimate speckle shifts associated with at least two regions of the tissue specimen.

16. A method of assessing a tissue sample, comprising:
measuring a first speckle shift associated with a first region of the tissue sample and a second speckle shift associated with a second region of the tissue sample; and
comparing the first speckle shift and the second speckle shift.

17. The method of claim 16, further comprising indicating an abnormality based on the comparison.

18. The method of claim 16, further comprising producing speckle patterns associated with the first speckle shift and the second speckle shift by propagating an acoustic wave in the tissue sample.

19. The method of claim 18, wherein the acoustic wave has a frequency of less than about 10 Hz.

20. The method of claim 19, wherein the acoustic wave is a surface wave.

21. An apparatus for determining specimen distortion, comprising:
a laser configured to provide component beams directed to the specimen so that the specimen is distorted;
a light source configured to illuminate the distorted specimen and produce a speckle pattern;
an image device configured to record a series of speckle pattern images; and
a processor configured to determine estimated speckle pattern images and provide an estimate of specimen distortion based on the series of estimated speckle pattern images.

22. The apparatus of claim 21, wherein the specimen is a cell.

23. The apparatus of claim 21, further comprising a flow chamber configured to provide the specimen in a fluid flow.

24. A method of determining a distortion of a specimen, comprising:
distorting the specimen with at least one light flux;
obtaining a speckle pattern image series based on a speckle pattern produced by the specimen, and based on the speckle pattern image series, produce estimated speckle pattern images; and
estimating a specimen distortion based on the estimated speckle pattern images.

25. The method of claim 24, wherein the specimen is distorted using two counter-propagating laser beams.

26. The method of claim 24, wherein the specimen is trapped with the light flux.

27. An apparatus for assessing elastic properties of a specimen, comprising:
an electro-acoustic transducer configured to produce an acoustic wave in the specimen;
a light source configured to deliver a light flux to the specimen and produce an optical speckle pattern that is recorded by an image capture device; and
a signal processor configured to receive a series of recorded optical speckle patterns and determine an optical speckle shift associated with the acoustic wave, wherein the signal processor is configured to determine optical speckle shifts associated with a plurality of specimen locations.

28. The apparatus of claim 27, further comprising a memory configured to store the series of recorded optical speckle patterns.

29. The apparatus of claim 27, further comprising a lens configured so that the optical speckle pattern recorded by the image capture device is an imaged optical speckle pattern.

30. The apparatus of claim 27, wherein the image capture device records two-dimensional optical speckle patterns.

31. The apparatus of claim 27, wherein the acoustic wave produced by the electro-acoustic transducer includes a surface acoustic wave.

32. The apparatus of claim 27, wherein the signal processor is configured to determine the optical speckle shift based on a maximum entropy method.

33. The apparatus of claim 27, wherein the signal processor is configured to determine the optical speckle shift based on a minimum mean square method.

34. An apparatus for assessing a tissue specimen, comprising:
a light source configured to illuminate the tissue specimen and produce optical speckle patterns;
an image capture device configured to record the optical speckle patterns;
an electro-acoustic transducer configured to produce an acoustic wave;
a speckle record processor configured to estimate speckle shifts in the optical speckle patterns produced by the acoustic wave; and
an indicator configured to provide an assessment metric based on the speckle shift, wherein the speckle record processor is configured to estimate speckle shifts associated with at least two regions of the tissue specimen and the assessment metric is based on a comparison of the speckle shifts.

35. An apparatus for assessing a tissue specimen, comprising:
a light source configured to illuminate the tissue specimen and produce optical speckle patterns;
an image capture device configured to record the optical speckle patterns;
an electro-acoustic transducer configured to produce an acoustic wave;
a speckle record processor configured to estimate speckle shifts in the optical speckle patterns produced by the acoustic wave, wherein the speckle record processor is configured to estimate speckle shifts associated with at least two regions of the tissue specimen.

* * * * *

UNITED STATES PATENT AND TRADEMARK OFFICE
CERTIFICATE OF CORRECTION

PATENT NO. : 7,088,455 B1 Page 1 of 1
APPLICATION NO. : 10/172754
DATED : August 8, 2006
INVENTOR(S) : Kirkpatrick et al.

It is certified that error appears in the above-identified patent and that said Letters Patent is hereby corrected as shown below:

In the Specification:

Column 4, line 36, "a screen a" should read --a screen--.

Column 4, line 57, "Eng" should read --Eng.--.

Column 7, line 66, "is two-dimensional" should read --is a two-dimensional--.

Column 11, line 58, "$j2\pi\delta x fk$" should read -- $j2\pi\delta x f_k$ --.

Column 14, lines 51-52, "element-by element" should read --element-by-element--.

In the Claims:

Column 16, line 14, "based" should read --based on--.

Signed and Sealed this

Sixth Day of March, 2007

JON W. DUDAS
*Director of the United States Patent and Trademark Office*